(12) United States Patent
Yilmaz

(10) Patent No.: US 11,589,617 B2
(45) Date of Patent: Feb. 28, 2023

(54) AEROSOL GENERATING DEVICE AND ARTICLE

(71) Applicant: BRITISH AMERICAN TOBACCO (INVESTMENTS) LIMITED, London (GB)

(72) Inventor: Ugurhan Yilmaz, London (GB)

(73) Assignee: Nicoventures Trading Limited, London (GB)

( * ) Notice: Subject to any disclaimer, the term of this patent is extended or adjusted under 35 U.S.C. 154(b) by 268 days.

(21) Appl. No.: 16/475,571

(22) PCT Filed: Dec. 20, 2017

(86) PCT No.: PCT/EP2017/083784
§ 371 (c)(1),
(2) Date: Jul. 2, 2019

(87) PCT Pub. No.: WO2018/127417
PCT Pub. Date: Jul. 12, 2018

(65) Prior Publication Data
US 2020/0383379 A1    Dec. 10, 2020

(30) Foreign Application Priority Data
Jan. 5, 2017 (GB) .................................... 1700136

(51) Int. Cl.
*A24F 40/46* (2020.01)
*A24F 40/44* (2020.01)
(Continued)

(52) U.S. Cl.
CPC .............. *A24F 40/44* (2020.01); *A24F 40/42* (2020.01); *A24F 40/46* (2020.01); *A24F 40/50* (2020.01);
(Continued)

(58) Field of Classification Search
None
See application file for complete search history.

(56) References Cited

U.S. PATENT DOCUMENTS

| 2,153,623 A | 4/1939 | Jacobson |
| 2,956,568 A | 10/1960 | Magnus et al. |
| (Continued) | | |

FOREIGN PATENT DOCUMENTS

| AR | 089648 A1 | 9/2014 |
| AR | 091949 A1 | 3/2015 |
| (Continued) | | |

OTHER PUBLICATIONS

International Search Report and Written Opinion, Application No. PCT/EP2017/083784, dated Jun. 20, 2018, 20 pages.
(Continued)

*Primary Examiner* — James Harvey
(74) *Attorney, Agent, or Firm* — Patterson Thuente, P.A.

(57) ABSTRACT

An aerosol generating device defines a flow path from an air inlet to an inhalable medium outlet. The device includes a container for containing a liquid; a wick for drawing liquid from the container into the flow path, and a heating element, upstream of the wick, for heating inlet air from the air inlet to generate a flow of heated air in the flow path in use. The device is arranged such that, in use, the flow of heated air generated in use passes over the wick to volatilize the liquid to generate, in use, a flow of aerosol in the flow path. The device includes a receiving portion in the flow path, downstream of the wick, for receiving an element for modifying a property of the flow of aerosol. A device including a shield element to shield the wick from a heating element is also disclosed.

22 Claims, 4 Drawing Sheets

(51) Int. Cl.
  *A24F 40/57* (2020.01)
  *A24F 40/42* (2020.01)
  *A61M 15/06* (2006.01)
  *A24F 40/50* (2020.01)
  *A24F 40/10* (2020.01)

(52) U.S. Cl.
  CPC ............. *A24F 40/57* (2020.01); *A61M 15/06* (2013.01); *A24F 40/10* (2020.01)

(56) References Cited

U.S. PATENT DOCUMENTS

| | | | |
|---|---|---|---|
| 3,339,557 A | 9/1967 | Karalus | |
| 3,468,316 A | 9/1969 | Baum et al. | |
| 4,038,994 A | 8/1977 | Aikman | |
| 4,227,540 A | 10/1980 | Edison | |
| 4,338,931 A | 7/1982 | Cavazza | |
| 4,478,228 A | 10/1984 | Chister | |
| 4,484,590 A | 11/1984 | Singh | |
| 4,559,955 A | 12/1985 | Brockway et al. | |
| 4,637,407 A | 1/1987 | Bonanno et al. | |
| 4,677,995 A | 7/1987 | Kallianos et al. | |
| 4,848,375 A | 7/1989 | Patron et al. | |
| 4,945,931 A | 8/1990 | Gori | |
| 4,991,605 A | 2/1991 | Keritsis | |
| 5,060,671 A | 10/1991 | Counts et al. | |
| 5,095,921 A | 3/1992 | Losee et al. | |
| 5,105,831 A | 4/1992 | Banerjee et al. | |
| 5,322,075 A | 6/1994 | Deevi et al. | |
| 5,408,574 A | 4/1995 | Deevi et al. | |
| 5,468,936 A | 11/1995 | Deevi et al. | |
| 5,573,692 A | 11/1996 | Das et al. | |
| 5,819,756 A * | 10/1998 | Mielordt | A61M 15/06 131/330 |
| 5,865,186 A | 2/1999 | Volsey, II | |
| 5,878,752 A | 3/1999 | Adams et al. | |
| 6,336,896 B1 | 1/2002 | Hsu et al. | |
| 6,382,465 B1 | 5/2002 | Greiner-Perth | |
| 6,606,992 B1 | 8/2003 | Schuler et al. | |
| 6,705,313 B2 | 3/2004 | Niccolai | |
| 6,708,846 B1 | 3/2004 | Fuchs et al. | |
| 7,374,063 B2 | 5/2008 | Reid | |
| 7,658,197 B1 | 2/2010 | Villagomez | |
| 8,377,009 B2 | 2/2013 | Sullivan et al. | |
| 8,997,753 B2 | 4/2015 | Li et al. | |
| 8,997,754 B2 | 4/2015 | Tucker et al. | |
| 9,004,073 B2 | 4/2015 | Tucker et al. | |
| 9,247,773 B2 | 2/2016 | Memari et al. | |
| 9,282,772 B2 | 3/2016 | Tucker et al. | |
| 9,693,587 B2 | 7/2017 | Plojoux et al. | |
| 10,010,687 B2 | 7/2018 | Von Schuckmann | |
| 10,426,199 B2 | 10/2019 | Turner et al. | |
| 10,470,491 B2 | 11/2019 | Sutton et al. | |
| 10,492,526 B2 | 12/2019 | Sampson et al. | |
| 10,758,686 B2 | 9/2020 | Reevell | |
| 2002/0079377 A1 | 6/2002 | Nichols | |
| 2003/0183616 A1 | 10/2003 | Goto | |
| 2004/0237974 A1 | 12/2004 | Min | |
| 2005/0000518 A1 | 1/2005 | Dunkley et al. | |
| 2005/0016533 A1 | 1/2005 | Schuler et al. | |
| 2005/0022813 A1 | 2/2005 | Alston | |
| 2005/0048003 A1 | 3/2005 | Ohki et al. | |
| 2005/0056280 A1 | 3/2005 | Alston et al. | |
| 2005/0081852 A1 | 4/2005 | Rangachari | |
| 2005/0126568 A1 | 6/2005 | Davies et al. | |
| 2005/0150492 A1 | 7/2005 | Dunkley et al. | |
| 2006/0272659 A1 | 12/2006 | Kobal et al. | |
| 2007/0012327 A1 | 1/2007 | Karles et al. | |
| 2008/0053465 A1 | 3/2008 | Tarora et al. | |
| 2008/0092912 A1 | 4/2008 | Robinson et al. | |
| 2010/0200006 A1 | 8/2010 | Robinson et al. | |
| 2011/0126848 A1 | 6/2011 | Zuber et al. | |
| 2013/0037041 A1 | 2/2013 | Worm et al. | |
| 2013/0037042 A1 | 2/2013 | Hearn et al. | |
| 2013/0042865 A1 | 2/2013 | Monsees et al. | |
| 2013/0068081 A1 | 3/2013 | Kronberg et al. | |
| 2013/0192615 A1 | 8/2013 | Tucker et al. | |
| 2013/0192616 A1 | 8/2013 | Tucker et al. | |
| 2013/0192619 A1 | 8/2013 | Tucker et al. | |
| 2013/0192620 A1 | 8/2013 | Tucker et al. | |
| 2013/0192621 A1 | 8/2013 | Li et al. | |
| 2013/0192622 A1 | 8/2013 | Tucker et al. | |
| 2013/0192623 A1 | 8/2013 | Tucker et al. | |
| 2013/0298905 A1 | 11/2013 | Levin et al. | |
| 2013/0312742 A1 | 11/2013 | Monsees et al. | |
| 2013/0333709 A1 | 12/2013 | Shimizu | |
| 2014/0060556 A1 | 3/2014 | Liu | |
| 2014/0202479 A1 | 7/2014 | Nicholls et al. | |
| 2014/0209105 A1 | 7/2014 | Sears et al. | |
| 2014/0366898 A1 | 12/2014 | Monsees et al. | |
| 2015/0027469 A1 | 1/2015 | Tucker et al. | |
| 2015/0027477 A1 | 1/2015 | Yoshino et al. | |
| 2015/0245654 A1 | 9/2015 | Memari et al. | |
| 2015/0245655 A1 | 9/2015 | Memari et al. | |
| 2015/0245656 A1 | 9/2015 | Memari et al. | |
| 2015/0245657 A1 | 9/2015 | Memari et al. | |
| 2015/0245662 A1 | 9/2015 | Memari et al. | |
| 2015/0245663 A1 | 9/2015 | Memari et al. | |
| 2015/0245664 A1 | 9/2015 | Memari et al. | |
| 2015/0245665 A1 | 9/2015 | Memari et al. | |
| 2015/0245666 A1 | 9/2015 | Memari et al. | |
| 2015/0245667 A1 | 9/2015 | Memari et al. | |
| 2015/0245668 A1 | 9/2015 | Memari et al. | |
| 2015/0272219 A1 | 10/2015 | Hatrick et al. | |
| 2015/0359266 A1 | 12/2015 | Memari et al. | |
| 2015/0374035 A1 | 12/2015 | Sanchez et al. | |
| 2016/0007648 A1 | 1/2016 | Sutton et al. | |
| 2016/0007649 A1 | 1/2016 | Sampson et al. | |
| 2016/0206005 A1 | 7/2016 | Yamada et al. | |
| 2016/0295922 A1 | 10/2016 | John et al. | |
| 2016/0324216 A1 | 11/2016 | Li et al. | |
| 2016/0331034 A1 | 11/2016 | Cameron | |
| 2016/0345632 A1 | 12/2016 | Lipowicz | |
| 2017/0055575 A1 | 3/2017 | Wilke et al. | |
| 2017/0055580 A1 | 3/2017 | Blandino et al. | |
| 2017/0055581 A1 | 3/2017 | Wilke et al. | |
| 2017/0055582 A1 | 3/2017 | Blandino et al. | |
| 2017/0055583 A1 | 3/2017 | Blandino et al. | |
| 2017/0055584 A1 | 3/2017 | Blandino et al. | |
| 2017/0071251 A1 | 3/2017 | Goch | |
| 2017/0086501 A1 | 3/2017 | Buehler et al. | |
| 2017/0238611 A1 | 8/2017 | Buchberger | |
| 2017/0245553 A1 | 8/2017 | Reevell | |
| 2017/0251723 A1 | 9/2017 | Kobal et al. | |
| 2017/0319799 A1 | 11/2017 | Yamada et al. | |
| 2017/0347706 A1 | 12/2017 | Aoun et al. | |
| 2018/0007966 A1 | 1/2018 | Li et al. | |
| 2018/0027882 A1 * | 2/2018 | Hepworth | A24F 40/42 |
| 2018/0221605 A1 | 8/2018 | Marks et al. | |
| 2018/0279678 A1 | 10/2018 | Hepworth et al. | |
| 2018/0360122 A1 | 12/2018 | Aoun et al. | |
| 2019/0098930 A1 | 4/2019 | Fallon et al. | |
| 2019/0124978 A1 | 5/2019 | Liu | |
| 2019/0125988 A1 | 5/2019 | Trzecieski | |
| 2019/0230990 A1 | 8/2019 | Hepworth | |
| 2019/0254343 A1 | 8/2019 | Hepworth et al. | |
| 2019/0254344 A1 | 8/2019 | Hepworth et al. | |
| 2019/0254345 A1 | 8/2019 | Hepworth et al. | |
| 2019/0254346 A1 | 8/2019 | Hepworth et al. | |
| 2019/0343182 A1 * | 11/2019 | Yilmaz | A61M 15/0003 |
| 2020/0060333 A1 | 2/2020 | Sutton et al. | |
| 2020/0367561 A1 | 11/2020 | Yilmaz et al. | |
| 2020/0376208 A1 | 12/2020 | Spencer et al. | |
| 2020/0383379 A1 * | 12/2020 | Yilmaz | A61M 11/042 |
| 2020/0390157 A1 | 12/2020 | Hepworth et al. | |
| 2020/0390158 A1 | 12/2020 | Hepworth et al. | |
| 2021/0100284 A1 | 4/2021 | Yilmaz et al. | |
| 2021/0322687 A1 | 10/2021 | Buchberger | |

FOREIGN PATENT DOCUMENTS

| | | |
|---|---|---|
| AU | 2013214984 A1 | 8/2014 |
| AU | 2013214987 A1 | 8/2014 |
| AU | 2013214991 A1 | 8/2014 |

(56) References Cited

FOREIGN PATENT DOCUMENTS

| | | |
|---|---|---|
| AU | 2013214993 A1 | 8/2014 |
| AU | 2013214994 A1 | 8/2014 |
| AU | 2013214997 A1 | 8/2014 |
| AU | 2013214998 A1 | 8/2014 |
| CA | 2845090 A1 | 2/2013 |
| CA | 2862105 A1 | 8/2013 |
| CA | 2862294 A1 | 8/2013 |
| CA | 2863185 A1 | 8/2013 |
| CA | 2863189 A1 | 8/2013 |
| CA | 2867620 A1 | 8/2013 |
| CA | 2867624 A1 | 8/2013 |
| CA | 2868313 A1 | 8/2013 |
| CA | 2980426 A1 | 10/2016 |
| CN | 2262810 Y | 9/1997 |
| CN | 2686350 Y | 3/2005 |
| CN | 2760984 Y | 3/2006 |
| CN | 101141892 A | 3/2008 |
| CN | 201108029 Y | 9/2008 |
| CN | 101277621 A | 10/2008 |
| CN | 201238609 Y | 5/2009 |
| CN | 101951796 A | 1/2011 |
| CN | 102258219 A | 11/2011 |
| CN | 102595943 A | 7/2012 |
| CN | 102781266 A | 11/2012 |
| CN | 103263083 A | 8/2013 |
| CN | 203369383 U | 1/2014 |
| CN | 203369386 U | 1/2014 |
| CN | 103859605 A | 6/2014 |
| CN | 203801735 U | 9/2014 |
| CN | 2038010735 | 9/2014 |
| CN | 104146352 A | 11/2014 |
| CN | 104219973 A | 12/2014 |
| CN | 104244749 A | 12/2014 |
| CN | 104244750 A | 12/2014 |
| CN | 104284606 A | 1/2015 |
| CN | 104287098 A | 1/2015 |
| CN | 104302197 A | 1/2015 |
| CN | 204104830 U | 1/2015 |
| CN | 104394722 A | 3/2015 |
| CN | 204191582 U | 3/2015 |
| CN | 204275207 U | 4/2015 |
| CN | 104661544 A | 5/2015 |
| CN | 204560971 U | 8/2015 |
| CN | 104968225 A | 10/2015 |
| CN | 204812043 U | 12/2015 |
| CN | 204812045 U | 12/2015 |
| CN | 204812046 U | 12/2015 |
| CN | 204812048 U | 12/2015 |
| CN | 204812049 U | 12/2015 |
| CN | 204888735 U | 12/2015 |
| CN | 105852229 A | 8/2016 |
| CN | 205492620 U | 8/2016 |
| CN | 106490692 A | 3/2017 |
| DE | 2548019 A1 | 5/1976 |
| DE | 3938634 A1 | 6/1990 |
| DE | 19645563 A1 | 5/1998 |
| DE | 102005016415 A1 | 11/2006 |
| EA | 201290586 A1 | 12/2012 |
| EA | 201490448 A1 | 12/2014 |
| EP | 0305788 A1 | 3/1989 |
| EP | 0317154 A1 | 5/1989 |
| EP | 0336458 A2 | 10/1989 |
| EP | 0430559 A2 | 6/1991 |
| EP | 0653898 A2 | 5/1995 |
| EP | 0914021 A2 | 5/1999 |
| EP | 1609376 A1 | 12/2005 |
| EP | 1555899 B1 | 12/2006 |
| EP | 1859694 A1 | 11/2007 |
| EP | 2083643 A1 | 8/2009 |
| EP | 2316286 A1 | 5/2011 |
| EP | 2327318 A1 | 6/2011 |
| EP | 2468117 A1 | 6/2012 |
| EP | 2723429 A1 | 4/2014 |
| EP | 2727619 A2 | 5/2014 |
| EP | 2740506 A1 | 6/2014 |
| EP | 2740507 A1 | 6/2014 |
| EP | 2740508 A1 | 6/2014 |
| EP | 2727619 A3 | 7/2014 |
| EP | 2756859 A1 | 7/2014 |
| EP | 2756860 A1 | 7/2014 |
| EP | 2809180 A1 | 12/2014 |
| EP | 2809182 A2 | 12/2014 |
| EP | 2809183 A1 | 12/2014 |
| EP | 2809184 A1 | 12/2014 |
| EP | 2809185 A1 | 12/2014 |
| EP | 2809186 A1 | 12/2014 |
| EP | 2809187 A1 | 12/2014 |
| EP | 2723429 A4 | 4/2015 |
| EP | 2809180 A4 | 7/2015 |
| EP | 2809184 A4 | 7/2015 |
| EP | 2809187 A4 | 7/2015 |
| EP | 2809182 A4 | 8/2015 |
| EP | 2809183 A4 | 8/2015 |
| EP | 2809185 A4 | 8/2015 |
| EP | 2809186 A4 | 9/2015 |
| EP | 2948006 A1 | 12/2015 |
| EP | 2964038 A1 | 1/2016 |
| EP | 2975956 A1 | 1/2016 |
| EP | 2989912 | 3/2016 |
| EP | 3039972 A1 | 7/2016 |
| EP | 3061358 A1 | 8/2016 |
| EP | 3100621 | 12/2016 |
| EP | 3245885 A1 | 11/2017 |
| GB | 607728 A | 9/1948 |
| GB | 2299012 A | 9/1996 |
| GB | 2446440 A | 8/2008 |
| GB | 2504075 A | 1/2014 |
| GB | 2504076 A | 1/2014 |
| GB | 201413018 | 9/2014 |
| GB | 201413019 | 9/2014 |
| GB | 201413021 | 9/2014 |
| GB | 201413025 | 9/2014 |
| GB | 201413027 | 9/2014 |
| GB | 201413028 | 9/2014 |
| GB | 201413030 | 9/2014 |
| GB | 201413032 | 9/2014 |
| GB | 201413034 | 9/2014 |
| GB | 201413036 | 9/2014 |
| GB | 201413037 | 9/2014 |
| GB | 2513061 A | 10/2014 |
| GB | 2523585 A | 9/2015 |
| GB | 2523585 A8 | 9/2015 |
| GB | 2524856 | 10/2015 |
| GB | 2525080 A | 10/2015 |
| GB | 2525294 A | 10/2015 |
| GB | 2525295 A | 10/2015 |
| GB | 2525480 A | 10/2015 |
| GB | 2525722 A | 11/2015 |
| GB | 2525723 A | 11/2015 |
| GB | 2525724 A | 11/2015 |
| GB | 2525725 A | 11/2015 |
| GB | 2525726 A | 11/2015 |
| GB | 2525727 A | 11/2015 |
| GB | 2529919 A | 3/2016 |
| GB | 2531633 A | 4/2016 |
| HK | 1197203 A1 | 1/2015 |
| HK | 1198138 A1 | 3/2015 |
| HK | 1198142 A1 | 3/2015 |
| HK | 1198143 A1 | 3/2015 |
| HK | 1200128 A1 | 7/2015 |
| HK | 1200129 A1 | 7/2015 |
| HK | 1203128 A1 | 10/2015 |
| IL | 233651 | 8/2014 |
| IL | 233896 | 9/2014 |
| IL | 230930 A | 6/2017 |
| IL | 233851 A | 6/2019 |
| IL | 233653 A | 4/2020 |
| IL | 233885 A | 5/2020 |
| IL | 233894 A | 5/2020 |
| IL | 233895 A | 5/2020 |
| JP | S5736898 U | 2/1982 |
| JP | S6033891 U | 3/1985 |
| JP | S649598 U | 1/1989 |
| JP | H0198470 A | 4/1989 |

(56) References Cited

FOREIGN PATENT DOCUMENTS

| | | |
|---|---|---|
| JP | H022331 A | 1/1990 |
| JP | H07192906 A | 7/1995 |
| JP | 3192677 B2 | 7/2001 |
| JP | 3325028 B2 | 9/2002 |
| JP | 3392138 B2 | 3/2003 |
| JP | 2006503572 A | 2/2006 |
| JP | 2006504431 A | 2/2006 |
| JP | 4324276 B2 | 9/2009 |
| JP | 2009213428 A | 9/2009 |
| JP | 2010506594 A | 3/2010 |
| JP | 2012075370 A | 4/2012 |
| JP | 2012135299 A | 7/2012 |
| JP | 2013509160 A | 3/2013 |
| JP | 2013519384 A | 5/2013 |
| JP | 2014524313 A | 9/2014 |
| JP | 2014532433 A | 12/2014 |
| JP | 2015503335 A | 2/2015 |
| JP | 2015505474 A | 2/2015 |
| JP | 2015505475 A | 2/2015 |
| JP | 2015505476 A | 2/2015 |
| JP | 2015506182 A | 3/2015 |
| JP | 2015508641 A | 3/2015 |
| JP | 2015512617 A | 4/2015 |
| JP | 2015513393 A | 5/2015 |
| JP | 2015513909 A | 5/2015 |
| JP | 2015516809 A | 6/2015 |
| JP | 2016509852 A | 4/2016 |
| JP | 2016517701 A | 6/2016 |
| JP | 2017511703 A | 4/2017 |
| JP | 2017512470 A | 5/2017 |
| KR | 20140070543 A | 6/2014 |
| KR | 20140090138 A | 7/2014 |
| KR | 20140125822 A | 10/2014 |
| KR | 20140125827 A | 10/2014 |
| KR | 20140125828 A | 10/2014 |
| KR | 20140125829 A | 10/2014 |
| KR | 20140127288 A | 11/2014 |
| KR | 20150003845 A | 1/2015 |
| KR | 20150005514 A | 1/2015 |
| KR | 20150018515 A | 2/2015 |
| KR | 20150035488 A | 4/2015 |
| MA | 20150054 A1 | 2/2015 |
| MA | 20150055 A1 | 2/2015 |
| MA | 20150056 A1 | 2/2015 |
| MA | 20150057 A1 | 2/2015 |
| MA | 20150058 A1 | 2/2015 |
| MA | 20150153 A1 | 5/2015 |
| MA | 20150169 A1 | 6/2015 |
| MX | 2014009396 A | 2/2015 |
| MX | 2014009398 A | 2/2015 |
| MX | 2014009393 A | 5/2015 |
| MX | 2014009394 A | 5/2015 |
| MX | 2014009397 A | 5/2015 |
| NZ | 627439 A | 9/2015 |
| NZ | 628058 A | 1/2016 |
| RU | 2015111364 A | 9/2015 |
| RU | 157882 U1 | 12/2015 |
| RU | 2581999 C2 | 4/2016 |
| RU | 2602964 C2 | 11/2016 |
| SG | 2014013627 A | 7/2014 |
| TW | 201315397 A | 4/2013 |
| WO | WO-9406314 A1 | 3/1994 |
| WO | WO-9527412 A1 | 10/1995 |
| WO | WO-02069745 A1 | 9/2002 |
| WO | WO-2004089126 A1 | 10/2004 |
| WO | WO-2006098171 A1 | 9/2006 |
| WO | WO-2007110650 A1 | 10/2007 |
| WO | WO-2009022232 A2 | 2/2009 |
| WO | WO-2010045671 A1 | 4/2010 |
| WO | WO-2011095410 A1 | 8/2011 |
| WO | WO-2011101164 A1 | 8/2011 |
| WO | WO-2012117578 A1 | 9/2012 |
| WO | WO-2012156695 A1 | 11/2012 |
| WO | WO-2013020280 A1 | 2/2013 |
| WO | WO-2013025921 A1 | 2/2013 |
| WO | WO-2013034459 A1 | 3/2013 |
| WO | WO-2013068081 A1 | 5/2013 |
| WO | WO-2013068100 A1 | 5/2013 |
| WO | WO-2013098405 A2 | 7/2013 |
| WO | WO-2013110211 A1 | 8/2013 |
| WO | WO-2013116558 A1 | 8/2013 |
| WO | WO-2013116561 A1 | 8/2013 |
| WO | WO-2013116565 A1 | 8/2013 |
| WO | WO-2013116567 A1 | 8/2013 |
| WO | WO-2013116568 A2 | 8/2013 |
| WO | WO-2013116571 A1 | 8/2013 |
| WO | WO-2013116572 A1 | 8/2013 |
| WO | WO-2013120566 A2 | 8/2013 |
| WO | WO-2013121608 A1 | 8/2013 |
| WO | WO-2013138384 A2 | 9/2013 |
| WO | WO 2013/155645 | 10/2013 |
| WO | WO-2013138384 A3 | 10/2013 |
| WO | WO-2013148810 A1 | 10/2013 |
| WO | WO-2013151295 A1 | 10/2013 |
| WO | WO-2013156339 A1 | 10/2013 |
| WO | WO-2013179524 A1 | 12/2013 |
| WO | WO-2014012905 A1 | 1/2014 |
| WO | WO-2014048745 A1 | 4/2014 |
| WO | WO-2014085719 A1 | 6/2014 |
| WO | WO-2014116974 A1 | 7/2014 |
| WO | WO-2014139611 A1 | 9/2014 |
| WO | WO-2014140273 A2 | 9/2014 |
| WO | WO-2014158051 A1 | 10/2014 |
| WO | WO-2013116568 A3 | 11/2014 |
| WO | WO-2014184239 A1 | 11/2014 |
| WO | WO-2015013108 A2 | 1/2015 |
| WO | WO-2015013108 A3 | 4/2015 |
| WO | WO-2015047954 A1 | 4/2015 |
| WO | WO-2015108816 A2 | 7/2015 |
| WO | WO-2015128665 A1 | 9/2015 |
| WO | WO-2015128666 A1 | 9/2015 |
| WO | WO-2015128667 A1 | 9/2015 |
| WO | WO-2016024083 A1 | 2/2016 |
| WO | WO-2016050244 A1 | 4/2016 |
| WO | WO-2016062777 A1 | 4/2016 |
| WO | WO-2016076178 A1 | 5/2016 |
| WO | WO-2016090426 A1 | 6/2016 |
| WO | WO-2016121143 A1 | 8/2016 |
| WO | WO-2016135342 A2 | 9/2016 |
| WO | WO-2016178377 A1 | 11/2016 |
| WO | WO-2016208759 A1 | 12/2016 |
| WO | WO-2017055514 A1 | 4/2017 |
| WO | WO-2017149152 A1 | 9/2017 |
| WO | WO-2017160559 A1 | 9/2017 |
| WO | WO-2017185051 A1 | 10/2017 |
| WO | WO-2018083037 A1 | 5/2018 |
| WO | WO-2018127417 A1 | 7/2018 |
| WO | WO-2019081571 A1 | 5/2019 |

OTHER PUBLICATIONS

Communication pursuant to Article 94(3) EPC for Application No. 1778008.3, dated Sep. 11, 2020, 8 pages.
Communication pursuant to Article 94(3) EPC for Application No. 17835844.6, dated Nov. 25, 2020, 5 pages.
Decision to Grant for Japanese Application No. 2015-559560, dated Apr. 4, 2017, 3 pages (6 pages with translation).
Decision to Grant dated Oct. 22, 2020 for Russian Application No. 2020118485, 9 pages.
Examination Report dated Oct. 26, 2017 for European Application No. 14717683.8, 5 pages.
Extended European Search Report for Application No. 18210216.0, dated May 9, 2019, 8 pages.
Extended European Search Report for Application No. 20210790.0, dated Feb. 18, 2021, 7 pages.
International Preliminary Report on Patentability for Application No. PCT/GB2014/050544, dated Sep. 11, 2015, 6 pages.
International Preliminary Report on Patentability for Application No. PCT/EP2017/073057, dated Mar. 28, 2019, 9 pages.
International Preliminary Reporton Patentability for Application No. PCT/EP2017/072811, dated Aug. 20, 2018, 7 pages.

(56) References Cited

OTHER PUBLICATIONS

International Preliminary Report on Patentability for Application No. PCT/EP2017/072814, dated Nov. 30, 2018, 8 pages.
International Preliminary Report on Patentability for Application No. PCT/EP2018/083665, dated Mar. 27, 2020, 15 pages.
International Preliminary Report on Patentability for Application No. PCT/GB2014/050545, dated Feb. 27, 2015, 5 pages.
International Preliminary Report on Patentability for Application No. PCT/EP2017/072813, dated Nov. 30, 2018, 9 pages.
International Preliminary Report on Patentability for Application No. PCT/EP2017/083785, dated Mar. 26, 2019, 17 pages.
International Preliminary Report on Patentability for Application No. PCT/EP2014/055485, dated Oct. 1, 2015, 11 pages.
International Preliminary Report on Patentabilityfor Application No. PCT/EP2017/073061, dated Mar. 28, 2019, 7 pages.
International Preliminary Report on Patentabilityfor Application No. PCT/EP2017/083784, dated Apr. 8, 2019, 23 pages.
International Search Report and Written Opinion for Application No. PCT/EP2014/055485, dated Jul. 31, 2014, 16 pages.
International Search Report and Written Opinion for Application No. PCT/EP2017/072811, dated Dec. 11, 2017, 15 pages.
International Search Report and Written Opinion for Application No. PCT/EP2017/072813, dated Dec. 11, 2017, 12 pages.
International Search Report and Written Opinion for Application No. PCT/EP2017/072814, dated Dec. 11, 2017, 12 pages.
International Search Report and Written Opinion for Application No. PCT/EP2017/073057, dated Feb. 7, 2018, 16 pages.
International Search Report and Written Opinion for Application No. PCT/EP2017/073061, dated Jan. 8, 2018, 13 pages.
International Search Report and Written Opinion for Application No. PCT/EP2017/083785, dated Apr. 9, 2018, 14 pages.
International Search Report and Written Opinion for Application No. PCT/GB2014/050544, dated Sep. 22, 2014, 7 pages.
International Search Report and Written Opinion for Application No. PCT/GB2014/050545, dated Oct. 8, 2014, 9 pages.
International Search Report for Application No. PCT/EP2018/083665, dated Mar. 13, 2019,5 pages.
International Search Report for Application No. PCT/EP2019/053821, dated May 24, 2019, 3 pages.
International Search Report for Application No. PCT/EP2019/053822, dated May 24, 2019, 3 pages.
Korean Office Action dated Oct. 26, 2020 for Korean Application No. 10-2019-7010642 27 pages.
Korean Office Action dated Oct. 26, 2020 for Korean Application No. 10-2019-7010644, 21 pages.
Notice of Allowance for Japanese Application No. 2015-559560, dated Mar. 27, 2017, 3 pages.
Notice of Reasons for Rejection for Japanese Application No. 2019-535975, dated Jul. 7, 2020,9 pages.
Notification to Grant Patent Right for Invention of Chinese Application No. 201480023894.4, dated Dec. 4, 2017, 5 pages.
Office Action dated Sep. 30, 2019 for Chinese Application No. 201480017532.4filed Mar. 19, 2014, 20 pages.
Office Action dated Sep. 8, 2020 for Japanese Application No. 2019-531421, filed Dec. 20, 2017, 16 pages.
Office Action for Chinese Application No. 201480023874.7, dated Mar. 30, 2018, 11 pages.
Office Action for Chinese Application No. 201480023894.4, dated Dec. 8, 2016, 8 pages.
Office Action for Chinese Application No. 2019-531415, dated Oct. 6, 2020, 12 pages.
Office Action for Japanese Application No. 2015-559559, dated Nov. 29, 2016, 4 pages (8 pages with translation).
Office Action for Japanese Application No. 2015-559560, dated Sep. 13, 2016, 4 pages (7 pages with translation).
Office Action for Japanese Application No. 2019-531421, dated Feb. 9, 2021, 14 pages.
Office Action For Korean Application No. 10-2019-7010649, dated Jan. 19, 2021, 7 pages.
Office Action dated Jan. 11, 2017 for Korean Application No. 10-2015-7025842, 25 pages (67 pages with translation).
Office Action dated Dec. 18, 2018 for Japanese Application No. 2017-172628, 4 pages.
Office Action dated Feb. 19, 2020 for Russian Patent Application No. 2019125438, 21 pages.
Office Action dated Aug. 20, 2020 for Russian Application No. 2019107330, 13 pages.
Office Action datedJul. 21, 2020 for European Application No. 17780009.1, 7 pages.
Office Action dated Jul. 21, 2020 for Japanese Application No. 2019-513761, 11 pages.
Office Action dated Jul. 21, 2020 for Japanese Application No. 2019-513827, 9 pages.
Office Action dated Jul. 21, 2020 for Japanese Application No. 2019-513842, 11 pages.
Office Action dated Dec. 22, 2020 for Korean Application No. 10-2019-7023118, 20 pages.
Office Action dated Aug. 23, 2016 for Japanese Application No. 2016-503647, 3 pages.
Office Action dated Jul. 7, 2020 for Japanese Application No. JP2019-513828, 12 pages.
Search report dated Sep. 23, 2019 for Chinese Application No. 201480017532.4 filed Mar. 19, 2014, 2 pages.
Search Report dated Mar. 2, 2018 for Great Britain Application No. GB1615609.3, 4 pages.
Written Opinion for Application No. PCT/EP2019/053821, dated May 24, 2019, 6 pages.
Written Opinion for Application No. PCT/EP2019/053822, dated May 24, 2019, 6 pages.
YE zonglin., "Household Electric Appliance Introduction," Light Industry Press, Mar. 1983, First Edition, pp. 74-78.
Office Action For Japanese Application No. 2020-529231, dated Jul. 20, 2021, 4 pages.
Application and File History for U.S. Appl. No. 15/733,181, filed Jun. 4, 2020, Inventor Yilmaz.
Examination Report for New Zealand for Application No. 764845, dated Nov. 17, 2021, 4 pages.
Office action for Korean Application No. 10-2020-7016127, dated Apr. 29, 2022, 26 pages.

* cited by examiner

AEROSOL GENERATING DEVICE AND ARTICLE

PRIORITY CLAIM

The present application is a National Phase entry of PCT Application No. PCT/EP2017/083784, filed Dec. 20, 2017, which claims priority from GB Patent Application No. 1700136.3, filed Jan. 5, 2017, each of which is hereby fully incorporated herein by reference.

TECHNICAL FIELD

The present disclosure relates to an aerosol generating device and an aerosol generating article.

BACKGROUND

Smoking articles such as cigarettes, cigars and the like burn tobacco during use to create tobacco smoke. Attempts have been made to provide alternatives to these articles that burn tobacco by creating products that release compounds without burning.

Examples of such products are so-called e-cigarette devices. These devices typically contain a liquid which is heated to vaporize the liquid to produce an inhalable vapor and/or aerosol. The liquid may contain nicotine and/or flavorings and/or aerosol-generating substances, such as glycerol. The known e-cigarette devices typically do not contain or use tobacco.

Other examples are heating devices which release compounds by heating, but not burning, the material. The material may be for example tobacco or other non-tobacco products, which may or may not contain nicotine.

SUMMARY

According to a first aspect of the present disclosure there is provided an aerosol generating device, the aerosol generating device defining a flow path from an air inlet to an inhalable medium outlet, the aerosol generating device comprising: a container for containing a liquid; a wick for drawing said liquid from the container into the flow path; a heating element, upstream of the wick, the heating element being for heating inlet air from the air inlet to generate, in use, a flow of heated air in the flow path; wherein the aerosol generating device is arranged such that, in use, said flow of heated air generated in use passes over the wick to volatilize said liquid to generate, in use, a flow of aerosol in the flow path; and further comprising a receiving portion in the flow path, downstream of the wick, the receiving portion being for receiving an element for modifying a property of said flow of aerosol passing therethrough in use.

The aerosol generating device may comprise a body, and an aerosol generating article releasably connected to the body, the body comprising the heating element and the aerosol generating article comprising the container.

The aerosol generating device may comprise a heating element controller to allow a user to control the degree to which inlet air from the air inlet is heated by the heating element in use.

The heating element may be arranged to heat inlet air so that a temperature, at the wick, of the flow of heated air generated in use is in the range 100° C. to 400° C., or within the range 150° C. to 300° C.

According to a second aspect of the present disclosure, there is provided an aerosol generating article for an aerosol generating device, the aerosol generating article defining a flow path from a heated air inlet for intake of a flow of heated air generated in use to an inhalable medium outlet, the aerosol generating article comprising: a container for containing a liquid; a wick, downstream of the heated air inlet, the wick being for drawing said liquid from the container into the flow path; wherein the aerosol generating article is arranged such that, in use, said flow of heated air generated in use passes over the wick to volatilize said liquid to generate, in use, a flow of aerosol in the flow path; and further comprising a receiving portion in the flow path, downstream of the wick, the receiving portion being for receiving an element for modifying a property of said flow of aerosol passing therethrough in use.

The aerosol generating article may be arranged to be releasably connectable to said aerosol generating device.

The aerosol generating device or aerosol generating article may be arranged such that, in use, the wick is heated only by, or substantially only by, convection.

The aerosol generating device or aerosol generating article may be arranged such that the wick is blocked from, or substantially blocked from, radiation generated by the heating element in use.

The aerosol generating device or aerosol generating article may comprise a shield element in the flow path, intermediate of the wick and the or a heating element for generating said flow of heated air in use, to shield the wick from the heating element.

The shield element may comprise a first element extending across a first portion of a cross section of the flow path.

The shield element may comprise a second element, downstream of the first element, extending across a second portion of said cross section of the flow path, at least some of which second portion is different from the first portion.

The second portion may be or comprise at least that portion of the cross section of the flow path across which the first element does not extend.

The shield element may extend across an entire cross section of the flow path, and comprise one or more perforations to allow air to pass through the shield element.

A portion of the wick exposed to said flow of heated air generated in use may be radially offset from a central longitudinal axis of the aerosol generating device or aerosol generating article.

The shield element may block a line of sight from the heating element to the wick.

The container may define a channel running therethrough, and the channel may define at least a portion of the flow path.

At least a portion of the channel may define the receiving portion.

The receiving portion may comprise one or more retaining elements for retaining said flavor element received in the receiving portion in use in the receiving portion.

The aerosol generating device or aerosol generating article may be arranged so as to allow said element received in the receiving portion in use to be manually inserted, removed and/or replaced in the receiving portion.

The wick may be or comprise a metal mesh.

The aerosol generating device or aerosol generating article may comprise an inlet controller to allow control of a flow of inlet air from the air inlet or the heated air inlet into the flow path.

The element may be received in the receiving portion.

The property may be one or more of an organoleptic property of the aerosol, a flavor of the aerosol, and the pH of the aerosol.

The element may be or comprise tobacco.

According to a third aspect of the present disclosure, there is provided an aerosol generating device, the aerosol generating device defining a flow path from an air inlet to an inhalable medium outlet, the aerosol generating device comprising: a container for containing a liquid; a wick for drawing said liquid from the container into the flow path; a heating element, upstream of the wick, the heating element being for heating inlet air from the air inlet to generate, in use, a flow of heated air in the flow path; and a shield element in the flow path, intermediate of the heater and the wick, to shield the wick from the heating element; wherein the aerosol generating device is arranged such that, in use, said flow of heated air generated in use passes over the wick to volatilize said liquid to generate, in use, a flow of aerosol in the flow path.

According to a fourth aspect of the present disclosure, there is provided an aerosol generating article for an aerosol generating device, the aerosol generating article defining a flow path from a heated air inlet for intake of a flow of heated air generated in use to an inhalable medium outlet, the aerosol generating article comprising: a container for containing a liquid; a wick, downstream of the heated air inlet, the wick being for drawing said liquid from the liquid container into the flow path; wherein the aerosol generating article is arranged such that, in use, the flow of heated air generated in use passes over the wick to volatilize said liquid to generate, in use, a flow of aerosol in the flow path; and a shield element in the flow path, upstream of the wick, to shield the wick from a heating element of said aerosol generating device generating said flow of heated air in use.

DETAILED DESCRIPTION

Figure 1:
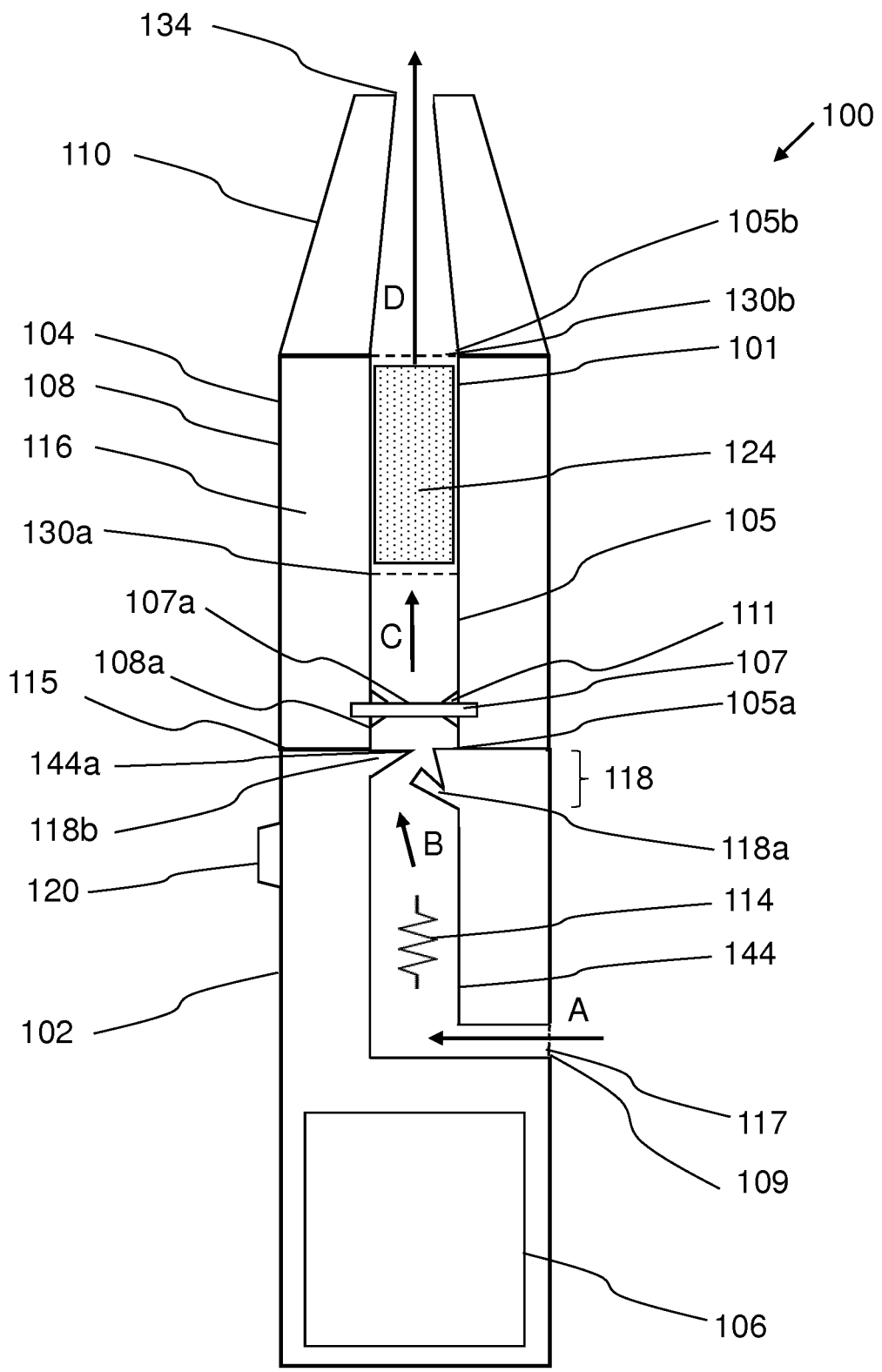
FIG. 1 illustrates a schematic cross section of a first aerosol generating device according to a first example.

Referring to FIG. 1, a schematic of an example aerosol generating device 100 according to a first example is illustrated. The aerosol generating device 100 is an inhalation device (i.e. a user uses it to inhale an aerosol provided by the device). The aerosol generating device 100 is hand-held.

The device 100 comprises a body 102 housing a power source 106 such as a battery 106, and a heating element 114.

The device 100 comprises a container 104. In this example, the container 104 is an aerosol generating article or cartridge 104 that is removable from the overall device 100. The cartridge 104 may therefore be installed, removed, or replaced in the device 100. The cartridge 104 comprises a connecting portion 115 for releasably connecting the cartridge 104 to the body 102 of the device 100. The cartridge 104 comprises a liquid container 108 for containing a liquid 116, and a wick 107 for drawing the liquid 116 from the liquid container 108. The cartridge 104 comprises a receiving portion 101. The receiving portion 101 has received therein an element 124 that modifies a property (for example flavor) of vapor or aerosol passing therethrough.

The device 100 comprises a mouthpiece 110 on which a user can draw. The mouthpiece 110 is removeably connected to the cartridge 104. The mouthpiece 110 defines an outlet 134 for egress of inhalable medium.

In broad outline, in the device 100 of FIG. 1, inlet air from an air inlet 109 in the body 102 of the device is heated by the heating element 114 to generate a flow of heated air. The wick 107 draws in liquid 116 from the liquid container 108, and the flow of heated air passes over the wick 107 to volatilize the liquid 116 thereby to generate a flow of at least one of a vapor and an aerosol. The flow of vapor or aerosol passes through the element 124 that modifies a property of the aerosol passing therethrough. For example, the element 124 may be a flavor element 124 for modifying (imparting) a flavor of (to) the vapor or aerosol passing therethrough. The vapor or aerosol, having passed through the flavor element 124, exits through the outlet 134 for inhalation by a user.

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A colloid is a substance in which microscopically dispersed insoluble particles are suspended throughout another substance.

For reasons of convenience, as used herein the term aerosol should be taken as encompassing an aerosol, a vapor or a mixture of an aerosol and vapor.

Returning to FIG. 1, the device 100 defines a flow path (illustrated schematically in FIG. 1 by arrows A to D) from the air inlet 109 in the body 102 of the device 100, via a channel 105 defined in the cartridge 104, to the inhalable medium outlet 134 defined in the mouthpiece 110.

The heating element 114 is located in a channel 144 defined by the body 102 of the device 100, the channel 144 extending from the air inlet 109 of the device 100 to a heated air outlet 144a of the body 102 of the device 100. The channel 144 of the body 102 defines at least a portion of the flow path (A-D) of the device 100.

The heating element 114 is (electrically) connected to the battery 106 to allow the heating element 114 to be powered. The heating element 114 may be controlled to be powered, for example, by a user pressing or interacting with a button or interface 120 of the body 102 of the device 100, and/or by a puff detector (not shown) of the overall device 100. The heating element 114 heats inlet air from the air inlet 109 of the device 100 to generate, in the flow path (A-D), a flow of heated air. Heated inlet air may exit the channel 144 of the body 102 via the heated air outlet 105a (and from there flow into the channel 105 of the cartridge 104).

In this example, the heating element 114 is located in the flow path (A-D), that is, the heating element 114 itself partially interrupts the flow path (A-D) such that the inlet air passes through, over and/or around the heating element 114. This may allow effective and/or efficient heating of the inlet air. The air inlet 109 comprises a mesh or filter element 117 to prevent dust or other particles or objects from being drawn in through the air inlet 109 and hence contacting the heating element 114.

The liquid container 108 is generally annular in shape, and defines the channel 105 running through the length of the liquid container 108, from a heated air inlet 105a to a modified aerosol outlet 105b. The channel 105 defines at least a portion of the first flow path (A-D). The liquid container 108 may be formed of rigid, watertight and airtight materials, such as metal, suitable plastics, etc.

The wick 107 is in contact with the liquid 116. This may be achieved for example by the wick 107 being inserted through a through hole (not shown) in a wall 108a of the liquid container 108 defining the channel 105. Alternatively or additionally, a portion of the wall 108a defining the channel 105 may be a porous member which allows liquid to pass through from the liquid container 108, and the wick 107 may be in contact with the porous wall 108a. The wall 108a may be for example in the form of a porous annulus. A porous wall 108a of this type may help to regulate the flow of liquid onto the wick 107. The wick 107 is generally absorbent and acts to draw in liquid 116 from the liquid container 108 by capillary action. The wick 107 can be non-woven.

The wick 107 extends across the channel 105. For example, the wick 107 may extend over substantially all of a cross section of the channel 105. The wick 107 may be or comprise a mesh (not shown), and may, for example, be formed of or comprise a metal mesh (not shown). Apertures (not shown) defined by the mesh (not shown) may allow heated air to flow through and around the mesh (not shown), thereby to volatilize the liquid 116 from the mesh to form an aerosol. The liquid 116 from the liquid container 108 may be drawn into the channel 105, by the mesh (not shown), for example by capillary action. Alternatively or additionally, the wick 107 may be or comprise for example a cotton or wool material or the like, or a synthetic material, including for example polyester, nylon, viscose, polypropylene or the like, or a ceramic material.

The wick 107 is supported in the channel 105 by a supporting element 111 that fixes and supports the wick 107 against the liquid container 108. This may help ensure the wick 107 does not move during use. The supporting element 111 may shelter an outer portion of the wick 107 from the heated air flow, hence leaving only a portion 107*a* of the wick 107 exposed in the channel 105.

A portion of the channel 105, downstream of the wick 107 (i.e. closer to the outlet, and further from the inlet, than the wick 107) defines a receiving portion 101. The receiving portion 101 has received therein an element 124 that modifies a property (for example flavor) of aerosol passing therethrough.

The receiving portion 101 is downstream of the wick 107 (i.e. closer to the outlet, and further from the inlet, than the wick 107). In this example, a portion of the channel 105 downstream of the wick 107 defines the receiving portion 101. The receiving portion 101 has received therein the element 124 that modifies a property (for example flavor) of aerosol passing therethrough.

The receiving portion 101 comprises one or more retainers 130*a*, 130*b* for retaining the element 124 in the receiving portion 101. A first retainer 130*a* is located in the channel 105 upstream of the element 124, and a second retainer 130*b* is located in the channel 105 downstream of the element 124. The first retaining element 130*a* may prevent the element 124 (or a portion thereof) from falling out of the receiving portion 101 and onto the wick 107. The second retaining element 130*b* may prevent the element 124 (or a portion thereof) from falling out of the receiving portion 101 and out of the outlet 134 of the mouthpiece 110.

Referring to the flow path (A-D), as the user draws on the aperture 134 defined by the mouthpiece 110, air is drawn through the air inlet 109 of the body 102 of the device 100, and into the channel 144 defined by the body 102 of the device 100 (shown in FIG. 1 by arrow A). The inlet air is drawn through, over and/or in and around the heating element 114, thereby to generate a flow of heated air (arrow B) in the channel 144 of the body. The flow of heated air is drawn from the heated air outlet 144*a* of the channel 144 of the body 102 of the device 100, into the heated air inlet 105*a* of the channel 105 of the cartridge 104. The heated air is drawn through, over and/or in and around the wick 107. The heated air volatilizes the liquid 116 on/in the wick 107 to generate a flow of aerosol in channel 105 (arrow C). The flow of aerosol is drawn through the channel 105 of the cartridge 104 into the receiving portion 101, via the first retaining element 130*a*. The flow of aerosol is drawn through the element 124 received in the receiving portion 101, which modifies a property of the aerosol, thereby generating a flow of modified aerosol. The modified aerosol is drawn through the second retaining element 130*b* of the receiving portion 101, out through the modified aerosol outlet 105*b* of the cartridge, into the mouthpiece 110, and out through an inhalable medium outlet 134 in the mouthpiece 110 for inhalation by the user (arrow D).

Passing heated inlet air over the wick 107 to generate an aerosol (i.e. generating aerosol by convection) may ensure uniformity or near uniformity of the temperature distribution along the wick 107 (as compared to, say, generating an aerosol by heating a wick using a wire heating element wrapped around the wick, for example). This may ensure that the liquid is volatilized uniformly across the wick 107, which may improve aerosol delivery and/or the consistency of aerosol delivery. This may also ensure that no one region of the wick 107 is heated to too high a temperature (i.e. ensure that no so-called "hot-spots" occur on the wick 107). This may reduce or avoid the generation of decomposition products of the liquid 116, such as carbonyls, which may be produced when the liquid 116 is heated to beyond a certain temperature. This may improve user experience. Passing heated inlet air over the wick 107 to generate an aerosol may also provide that the wick 107 remains at a substantially constant temperature in use regardless of whether the wick 107 is wet with liquid 116 or dry. This may reduce or avoid the generation of decomposition products, such as carbonyls, of the liquid 116 on the wick 107 which may be produced when the liquid 116 is heated to beyond a certain temperature. This may improve user experience. The wick 107 being formed of a metal mesh (or another suitably thermally conductive material) may also improve the uniformity of the temperature distribution across the wick 107, and hence help reduce or avoid production of decomposition products mentioned above.

The heating element 114 being housed in the body 102 of the device 100 (rather than, for example, in the cartridge 104) may reduce the production cost of the cartridge 104, which may, for example, be disposable (i.e. a consumable). This also may allow a larger and/or more powerful heating element 114 to be used which may heat inlet air faster and/or to a higher temperature and hence volatilize more liquid (or volatilize liquid more quickly), and/or to release more constituents (or release constituents more quickly) from the element 124. This may improve user experience.

The device 100 may comprise a heating element controller (e.g. button 120) to allow a user to control of the degree to which inlet air from the air inlet 109 is heated by the heating element 114. For example, the button or interface 120 of the body 102 of the device 100 may be arranged to allow a user to set a setting of the heating element 114. For example, this setting may correspond to the current running through the heating element 114. The settings may range, for example, from an "off" setting in which the heating element 114 does not heat inlet air, to a "maximum" setting corresponding to a predetermined maximum heating of inlet air by the second heating element 114, and/or any other intermediate setting. The predetermined "maximum" setting may help ensure that aerosol is not heated to a too high temperature (for example to avoid degradation of the liquid 116), that the element 124 is not heated to a too high temperature (for example to avoid combustion of the element 124) and that the inhalable medium exiting the device 100 is a safe and comfortable temperature for the user, for example. This may ensure safe delivery of the inhalable medium. Alternatively or additionally a "boost" setting or button may be provided to allow a user to increase heating of inlet air (and hence increase aerosol delivery and/or increase release of constituents from the element 124) for a user specified or predetermined period of time. A user may thereby temporarily "boost" a flavor of the inhalable medium produced by the device 100, for example. This control may allow a user flexibility to control the properties and/or composition of the inhalable medium produced by the device 100, and therefore may improve user experience.

The heating element 114 (and/or the control thereof) may be arranged to heat inlet air so that a temperature, at the wick 107, of the flow of heated air generated in use is in the range 100° C. to 400° C., for example in the range 150° C. to 300° C. This temperature may be sufficient to volatilize known e-liquids, and hence produce a flow of aerosol in the flow path (A-D).

The device 100 and/or cartridge 104 may be arranged such that in use the flow of aerosol (and heated air into which the aerosol is entrained) heats at least an outer portion of the element 124 received in the receiving portion 101 to a temperature in the range 30° C. to 150° C., for example in the range 40° C. to 120° C. These temperatures may encourage the release of constituents of the element 124 into the aerosol, but may not combust the element 124. These temperature ranges are examples, and it will be appreciated that any increase in temperature of the element 124 above an ambient temperature may encourage release of constituents from the element 124.

In this example, the cartridge 104 is elongate, and extends along the length of the device 100. The channel 105 through which the aerosol flows, and which defines the receiving portion 101, is defined by the liquid container 118. This arrangement is particularly space efficient. This may reduce the size and production cost of the cartridge 104 and/or the device 100.

The device 100 and/or the cartridge 104 may comprise an inlet controller (not shown) to allow a user to control a flow of inlet air from the air inlet 109 of the device 100 (and/or the heated air inlet 105a of the cartridge 104) into the flow path (A-D). This may allow the rate, for a given draw, of air flowing over the heating element 114 to be varied. This may allow user control of the degree to which inlet air is heated. This flexibility may improve user experience.

The device 100 and/or cartridge 104 may be arranged so as to allow the element 124 received in the receiving portion 101 in use to be manually inserted, removed and/or replaced in the receiving portion 101. For example, the second retaining element 130b of the cartridge may not be present, or may be removable. A user may therefore remove the mouthpiece 101 from the cartridge 104 (and remove the second retaining element 130b if present) to gain access to the receiving portion 101, and thereby manually insert, remove and or replace an element 124 therein. This flexibility may allow a user to customize the inhalable medium produced by the device 100, and hence may improve user experience. This may also allow a user to replace the element 124 at a different rate to the replacement of the cartridge 104 as a whole, which may be useful for example if the element 124 is used or degrades before the liquid 116 is used or degrades. This may improve user experience.

In other examples, the cartridge 104 may be disposable, and the cartridge 104 may be sealed on production and thereby arranged not to allow the element 124 to be manually inserted into and/or manually removed from the receiving portion 101 in use. Similarly, the liquid container 108 may be sealed on production and thereby arranged not to allow the liquid 116 to be replaced. This may reduce production costs of the cartridge 104. This may also help prevent leakage of one or both of the liquid 116 and the element 124 from the cartridge 104, and hence provide for a clean and reliable inhalable medium delivery.

The element 124 may be or comprise material that may be used to impart a flavor (and/or one or more other constituents) to the aerosol (and heated air in which the aerosol is entrained) passing therethrough. In some examples, one or more constituents of the element 124 may be constituents inherent to the material itself. The material may for example consist of or comprise tobacco. As the aerosol passes through and over the tobacco, the aerosol entrains organic and/or other compounds or constituents from the tobacco that lend tobacco its organoleptic properties, thus imparting flavor to the aerosol. It will be understood however that materials other than tobacco may be used to impart different flavors (and/or one or more other constituents) to the aerosol. The element 124 may comprise constituents added to a material of the element 124.

Nicotine may be provided in the liquid 116, may be obtained from the element 124, or any combination of these. Flavorings may be added to the element 124 (whether or not the element 124 is or includes tobacco) and/or to the liquid 116. A material of the element 124 may be a solid material, or be a mixture of solid materials, one or more of each comprising one or more constituents that can be mixed with the aerosol. It will be appreciated that the element 124 may comprise one or more other constituents that are not entrained into the aerosol passing therethrough. It will also be appreciated that the element 124 may comprise a portion that does not impart any flavor to and/or release any constituents into and/or modify any property of the aerosol flow.

The element 124 may be porous, for example so as allow aerosol to pass through it. The element 124 may be self-supporting, so as to be easily handled by a user (for example easily inserted and/or removed from the receiving portion 101 where the receiving portion 101 allows for this). For example the element 124 may comprise material wrapped partially or wholly in a wrapper, and/or the element 124 may be supported in a resilient housing, for example a plastic housing (not shown). The element 124 may comprise, for example, a flavored carrier material, such as cellulose acetate or the like. The element 124 may be shaped so as to fit easily and/or tightly into a correspondingly shaped receiving portion 101.

The element 124 may be for modifying a property of the heated inlet air other than (or in addition) to flavor, for example it could comprise a substance for modifying a property of the heated air other than (or in addition) to flavor.

In some examples, the element 124 may comprise a substance that modifies one or more other organoleptic properties of aerosol (e.g. modifying the feel or smell or look of the aerosol to the user). In some examples, the element 124 may comprise a substance that modifies the nicotine content of the aerosol flow passing therethrough. In some examples, the element 124 may comprise a substance that modifies the PH of the aerosol by either lowering or raising the PH (e.g. modifying the acidity or the basicity of the aerosol). In some examples, the element 124 may comprise a substance that modifies (e.g. reduce) the amount of aldehydes in the aerosol. In some examples, the element 124 may comprise a substance that modifies different combinations of two or more of these or indeed other properties of the aerosol.

The device 100 comprises a shield element 118 located in the channel 144 defined by the body 102 of the device 100. The shield element 118 is located intermediate of the wick 107 and the heating element 114 in the flow path (A-D) so as to shield the wick 107 from the heating element 114. The wick 107 is thereby substantially blocked, by the shield element 118, from radiation generated by the heating element 114. Accordingly, the wick 107 is heated only by, or substantially only by, convection. This may help ensure the advantages of producing aerosol by convention mentioned above. The shield element 118 may alternatively or additionally prevent or reduce liquid 116 leaking from the wick 107 onto the heating element 114. This may prevent damage to and/or degradation of the heating element 114, and hence improve the longevity of the heating element 114 and hence the overall device 100. This may also reduce or prevent the generation of decomposition products, such as carbonyls, or other products, of the liquid 116 which may be produced when the liquid 116 is heated to beyond a certain temperature if directly contacting the heating element 114.

In this example, the shield element 118 comprises a first element 118a extending across a first portion of a cross section of the channel 144. The shield element 118 comprises a second element 118b, downstream of the first element 118a, extending across a second portion of the cross section of the channel 144. The first element 118a and the second element 118b are located on opposite sides of the channel 144. The second portion of the cross section across which the second element 118b extends comprises that portion of the cross section across which the first element 118a does not extend. As a result, shield element 118 ensures there is no line-of-sight between the heating element 114 and the heated air outlet 144a of the body 102 of the device 100. The shield element 108 therefore blocks the wick 107, or at least the exposed portion of the wick 107a, from radiation from the heating element 114. This helps ensure that the wick 107 is heated by convection only. This arrangement may also help to prevent or reduce liquid 116 leaking from the wick 107 onto the heating element 114.

The first element 118a and the second element 118b are angled with respect to the flow direction in the channel 144 such that they extend towards the heated air outlet 144a of the channel 144 (i.e. extend in the direction of flow of the flow path (A-D)). This may promote flow of heated air downstream in the device 100, and inhibit flow of aerosol into the channel 144.

In the above example described with reference to FIG. 1, the shielding element 118 comprised a first element 118a and a second element 118a extending from opposite sides of the channel 144 of the body 102 of the device 100. However, this need not necessarily be the case.

Figure 2:
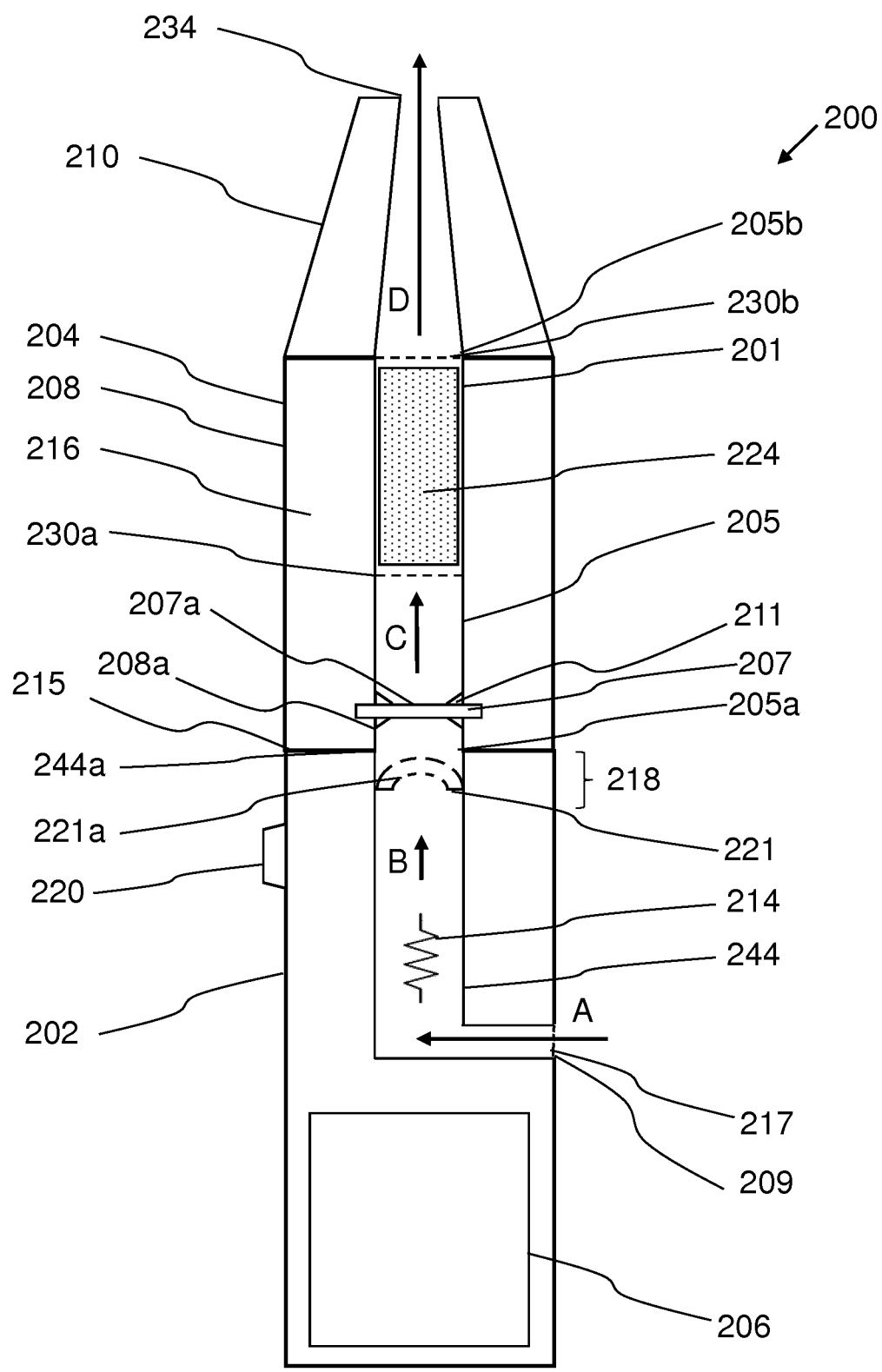
FIG. 2 illustrates a schematic cross section of a second aerosol generating device according to a second example.

FIG. 2 illustrates a device 200 according to another example. The device 200 is exactly the same as the device 100 described with reference to FIG. 1, except for the shield element 218. For brevity, features in FIG. 2 and the functioning thereof that are the same as those features already described with reference to FIG. 1 are given similar reference numerals to those in FIG. 1 but increased by 100, and will not be described again.

As illustrated in FIG. 2, the shield element 218 of the device 200 comprises an element 221 that extends across the entire cross section channel 244 of the body 202 of the device 200. The element 221 is arcuate in cross-section, and protrudes towards the heated air outlet 244a of the channel 244 (i.e. protrudes in the direction of flow of the flow path (A-D)). The element 221 comprises one or more perforations 221a to allow air to pass through the element 221. This arrangement provides a simple way to block or reduce radiation from the heating element 214 from reaching the wick 207 (and to prevent or reduce liquid 216 leaking from the wick 207 onto the heating element 214). The simplicity of the construction leads to reduced production costs.

Figure 3:
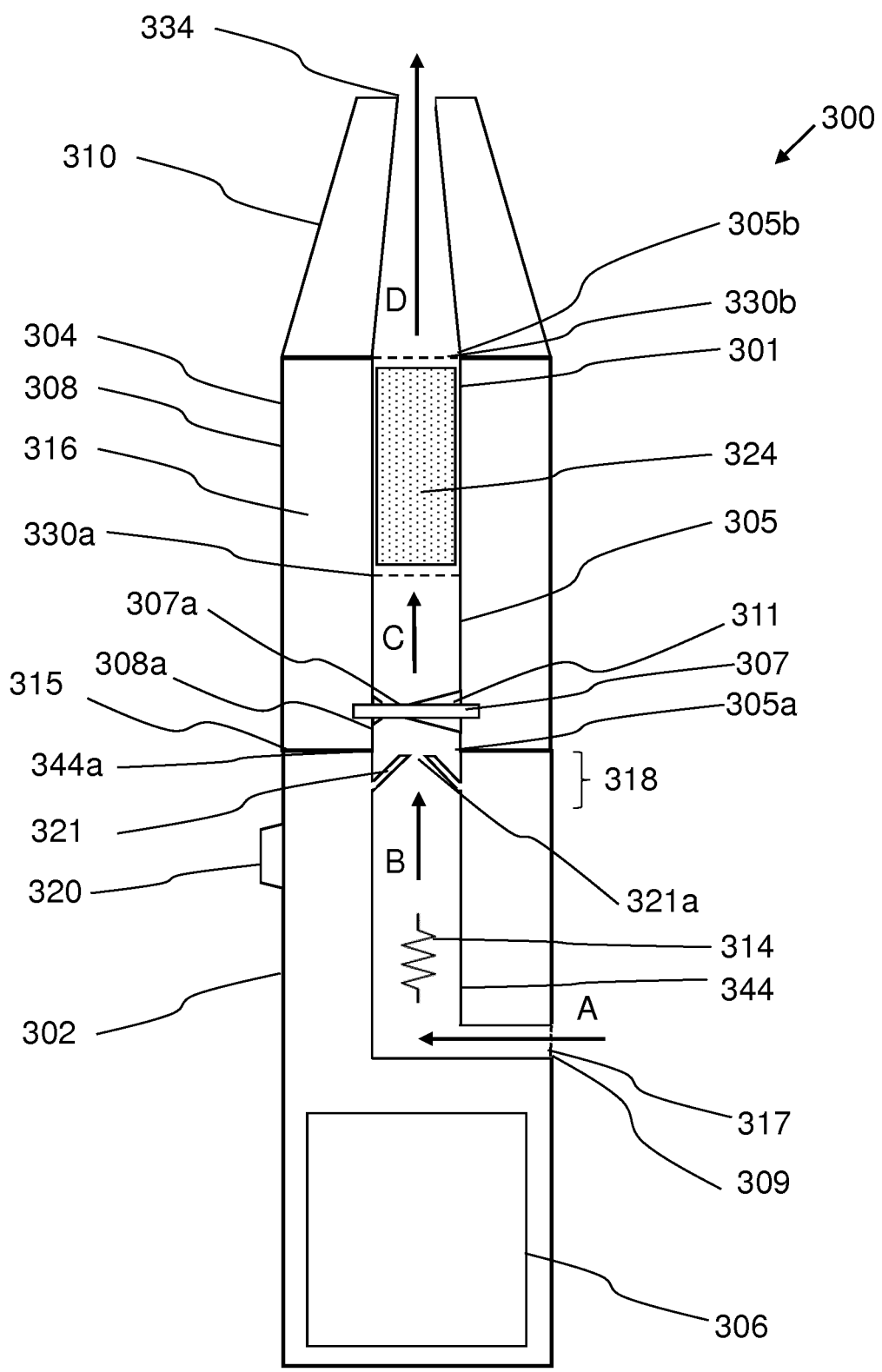
FIG. 3 illustrates a schematic cross section of a third aerosol generating device according to a third example.

FIG. 3 illustrates a device 300 according to another example. The device 300 is exactly the same as the device 200 described with reference to FIG. 2, except for the shield element 218 and the configuration of the wick 307. For brevity, features in FIG. 3 and the functioning thereof that are the same as those features already described with reference to FIG. 2 are given similar reference numerals to those in FIG. 2 but increased by 100, and will not be described again.

As illustrated in FIG. 3, the shield element 318 comprises an element 321 that extends across the entire cross section of the channel 344 of the body 302 of the device 300. The element 321 defines an aperture 320a in its centre to allow air to pass through the element 321. The element 321 protrudes in the channel 344 towards the heated air outlet 344a of the channel 344 (i.e. protrudes in the direction of flow of the flow path (A-D)). The wick 307 extends laterally across the channel 305 of the cartridge 304. The supporting element 311 supports and shelters an outer portion of the wick 307 from the heated air flow, hence leaving only a portion 307a of the wick 307 that does not coincide with the supporting element 322 and hence is exposed in the channel 105. However, the wick 307 and the supporting element 311 are arranged such that the portion 307a of the wick 307 exposed to the flow of heated air flowing through the channel 305 of the cartridge 304 is radially offset from the central longitudinal axis of the cartridge 304, that is radially offset with respect to the aperture 321a in the shield element 318. This offset arrangement provides that there is no line-of-sight between the heating element 314 and the exposed portion 307a of the wick 307, and hence may ensure that the aerosol production at the wick is only by convection, or substantially only by convection. This arrangement may also help prevent or reduce liquid 316 leaking from the wick 307 onto the heating element 314. This arrangement may provide less resistance to the flow in the flow path (A-D).

Figure 4:
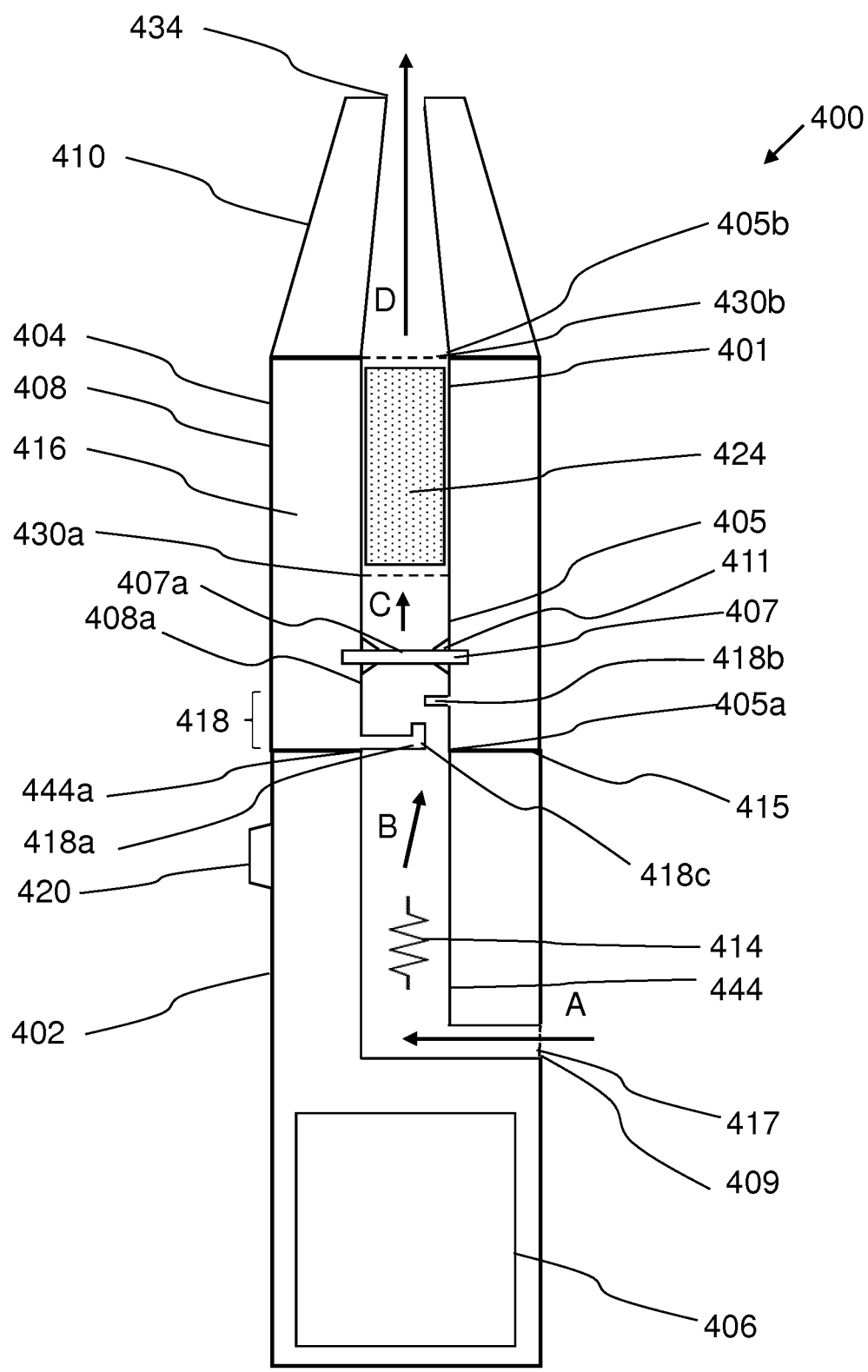
FIG. 4 illustrates a schematic cross section of a fourth aerosol generating device according to a fourth example.

FIG. 4 illustrates a device 400 according to another example. The device 400 is exactly the same as the device 300 described with reference to FIG. 3, except for an alternative arrangement and placement of the shield element 318. For brevity, features in FIG. 4 and the functioning thereof that are the same as those features already described with reference to FIG. 3 are given similar reference numerals to those in FIG. 3 but increased by 100, and will not be described again.

As illustrated in FIG. 4, the shield element 418 is located in the channel 405 of the cartridge 404. The shield element 418 comprises a first element 418a extending across a first portion of a cross section of the channel 405 of the cartridge 404. The shield element 418 comprises a second element 418b, downstream of the first element 418a, extending across a second portion of the cross section of the channel 405. The first element 418a and the second element 418b are located on opposite sides of the channel 405. The second portion of the cross section over which the second element 418b extends comprises that portion of the cross section across which the first element 418a does not extend. In other words, the shield element 418 is in a staggered arrangement, and comprises the first element 418a and the second element 418b in a staggered with respect to one another along the channel 405 of the cartridge 404. As a result, the shield element 418 ensures there is no line-of-sight between the heating element 414 and the wick 407. This helps ensure that the wick 407 is heated by convection only. It will be appreciated that although two shield elements 418a, 418b are shown in FIG. 4, there may be more than two, for example staggered with respect to one another along the channel 405 of the cartridge 404.

An end portion 418c of the first element 418a extends substantially parallel with respect to the flow direction in the channel 444 such that it extends away from the heated air inlet 405a of the channel 405 of the cartridge 404. This may promote flow of heated air downstream in the device 100, and inhibit flow of aerosol into the channel 444 of the body 402 of the device 400. This arrangement may also prevent or reduce liquid 416 leaking from the wick 407 onto the heating element 414. It will be appreciated that the end portion 418c of the first element 418a need not necessarily extend substantially parallel with respect to the flow direction in the channel 444 and may instead be angled with respect to the flow direction in the channel 444 such that it extends at least partially away from the heated air inlet 405a of the channel 405 of the cartridge 404.

Although the examples above referred to use of a device 100, 200, 300 with a cartridge 104, 204, 304 it will be readily appreciated that there are many configurations of aerosol generating devices (some of which not having cartridges as such, but rather, for example, refillable liquid containers integral to the device 100) and that the above examples may also be applied to these or other configurations. For example, the cartridge 104, 204, 304 may be integral to the device 100, 200, 300, and for example the liquid container 118, 218, 318 may be refillable, and the receiving portion 101, 201, 301 may be accessible by a user to remove, insert of replace an element 124, 224, 324 into the receiving portion 101, 201, 301. In some examples, the mouthpiece 110, 210, 310, etc., is not removable from the cartridge 104, 204, 304, etc., and may instead be formed integrally with the cartridge 104, 204, 304, for example.

In any of the examples described above, a device controller (not shown) may control operation of the device as a whole. Operation of one or more of the heating elements 112, 114, 212, 214, 312 may be controlled so that the liquid 116, 216, 316 and/or material of the element 124, 224, 324 is heated to an optimum temperature. Particular considerations include ensuring that the element 124, 224, 324 does not burn, ensuring that adequate vaporization of the liquid 116, 216, 316 is achieved, and ensuring that inhalable medium produced is at a comfortable and safe temperature for the user. As mentioned above, a puff detector, a device which is known per se, may be provided to signal to the controller when one or more of the heating elements needs to be energized. Alternatively or additionally, the user may control the device via controls or an interface 120, 220, 320, which may be external to the overall device 100, 200, 300, for example via radio control signals, or Bluetooth or the like from a separate control device, such as a smartphone or the like.

Suitable example liquids 116, 216, 316 include those conventionally used in e-cigarette devices, including for example propylene glycol and glycerol (also known as glycerin). Also as described in relation to the examples above, the element 124, 224, etc., may be or comprise a material that may be used to modify a property, such as a flavor, of the heated air passing therethrough. For example, the material may comprise constituents that impart cooling sensations, heating sensations, nutraceutical benefits, stimulating benefits or produce or induce any other sensation or benefit in the user. The material may for example consist of or comprise tobacco. As aerosol passes through and over the tobacco material, the air may entrains organic and other compounds or constituents from the tobacco material that lend tobacco its organoleptic properties, thus imparting the flavor to the aerosol as it passes to the mouthpiece. Materials other than tobacco may be used to impart different flavors to the aerosol. For example, materials other than tobacco may be blended with tobacco, or blends of other materials such as, for example, vanilla pods, star anise, mint leaves, other herbs, and the like. For example, flavorants could be included in the material or in the liquid 116, 216, etc., or both. In the example where flavorants are included in both the element 124, 224, etc., and the liquid 116, 216, etc., the generated aerosol may be flavored with a first flavor, and the flavor element 124, 224, etc., may impart a second flavor to the aerosol passing therethrough, thereby to generate an inhalable medium having the first and the second flavors. The first flavor and the second flavor may be the same, in which case the element 124, 224, etc., may act so as to enhance the perceived flavor of the aerosol. The first flavor and the second flavor may be different, in which case the element 124, 224, 324 may act so as to alter the perceived flavor of the aerosol. The user may therefore easily customize the flavor of the inhalable medium exiting the device 100, 200, etc. The element 124, 224, etc., may be a nicotine source that is intended to provide nicotine substantially without any flavor.

The element 124, 224, 324 may be or comprise any tobacco-containing material and may, for example, include one or more of tobacco per se, different varieties of tobacco, tobacco derivatives, pelletized tobacco, extruded tobacco, expanded tobacco, reconstituted tobacco, ground tobacco, tobacco extract, homogenized tobacco or tobacco substitutes. In the case of tobacco, the material may be in the form of a rod of tobacco, a pod or plug of tobacco, loose tobacco, agglomerates, etc., and may be in relatively dry form or in relatively moist form for example. The tobacco may have been modified, for example chemically modified, for example had its pH modified so as to promote the release of selected constituents of the tobacco such as nicotine. Suitable solid materials may include other, non-tobacco, products, which, depending on the product, may or may not contain nicotine. A tobacco rod may be formed using a wrapping material.

As used herein, the terms "flavor" and "flavorant" may refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, solid, or powder. For example, a liquid, oil, or other such fluid flavorant may be impregnated in a porous solid material of the element 124, 224, 324 so as to impart flavor and/or other properties to that porous solid material. As such, the liquid or oil is a constituent of the material in which it is impregnated.

The above embodiments are to be understood as illustrative examples of the disclosure.

For example, in some examples, the second retaining element 130*b*, 230*b*, 330*b*, 430*b* is part of or removeably connected to the mouthpiece 110, 210, 310, 410 instead of the cartridge 104, 204, 304, 404. In some other examples, there are no retaining elements 130*a*, 130*b*, 230*a*, 230*b*, etc., and the element 134, 234, etc., may be held in the receiving portion 101, 201, 301 for example, via a interference fit, or via contact with a lip (not shown) at either end of the channel 105, 205, 305 for example. In some examples, the cartridge 104, 204, 304 or a portion thereof may itself act as a mouthpiece 110, 210, 310, or an alternative mouthpiece 110, 210, 310 may be provided. In some examples, there is no mesh or filter element 117, 217, 317, 417 across the air inlet 109, 209, 309, 400.

Although in the above examples the device 100, 200, 300, etc., or cartridge 104, 204, 304 is described as comprising a receiving portion 101, 201, 301 for receiving an element 124, 224, 324, in some other examples, this need not necessarily be the case, and the device 100, 200, 300, etc., or cartridge 104, 204, 304 need not comprise a receiving portion 101, 201, 301. In these examples, the aerosol generated at the wick 107, 207, 307 need not pass through an element 124, 224, 324 before inhalation by a user. It will therefore be appreciated that, in some examples, the aerosol generating device 100, 200, 300, etc., and/or the aerosol generating article 104, 204, 304, etc., described above may comprise the shield element 118, 218, 318, etc., but may not comprise a receiving portion 101, 201, 301 or an element 124, 224, 324 received therein.

Although in the above examples the shield element 118, 218, 318, 418 was described as comprising elements 118*a*, 118*b*, 418*a*, 418*b* protruding into the flow path (A-D) or an element 221, 321 extending across the flow path (A-D), this need not necessarily be the case and in other examples the shield element 118, 218, 318, 418 may take other forms that may ensure that the wick 107, 207, 307 is blocked from the radiation of the heating element 114, 214, 314, 414 and/or that may ensure the wick 107, 207, 307 is heated substantially only by convection, for example. For example, the shield element 118, 218, 318 may alternatively or additionally be or comprise a bend or elbow in the flow path (A-D), for example a bend or elbow in the channel 144, 244, 344, 444 of the body 102, 202, 302, 402 of the device 100, 200, 300, 400, the bend or elbow being intermediate of the heating element 114, 214, 314, 414 and the wick 107, 207, 307, 407.

Although in the above examples, the device 100, 200, 300, 400 was described as comprising a shield element 118, 218, 318, 418 (for example located in the body 102, 202, 302, 402 or the cartridge 104, 204, 304, 404 of the device 100, 200, 300, 400) this need not necessarily be the case and in other examples the device 100, 200, 300, 400 does not comprise a shield element 118, 218, 318, 418 that blocks the wick 107, 207, 307, 407 from the radiation of the heating element 114, 214, 314, 414.

It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the invention, which is defined in the accompanying claims.

The invention claimed is:

1. An aerosol generating device, the aerosol generating device defining a flow path from an air inlet to an inhalable medium outlet, the aerosol generating device comprising:
   a container for containing a liquid;
   a wick for drawing the liquid from the container into the flow path;
   a heating element upstream of the wick, the heating element being for heating inlet air from the air inlet to generate, in use, a flow of heated air in the flow path, wherein the aerosol generating device is arranged such that, in use, the generated flow of heated air passes over the wick to volatilize the liquid to generate a flow of aerosol in the flow path; and
   a receiving portion in the flow path downstream of the wick, the receiving portion being for removably receiving an element for modifying a property of the flow of aerosol passing therethrough in use, wherein the property is one or more of an organoleptic property of the aerosol, a flavor of the aerosol, or a pH of the aerosol.

2. The aerosol generating device according to claim 1, further comprising a body, and an aerosol generating article releasably connected to the body, the body comprising the heating element and the aerosol generating article comprising the container.

3. The aerosol generating device according to claim 1, further comprising a heating element controller to allow a user to control a degree to which inlet air from the air inlet is heated by the heating element in use.

4. The aerosol generating device according to claim 1, wherein the heating element is arranged to heat inlet air so that a temperature, at the wick, of the flow of heated air generated in use is in a range 100° C. to 400° C.

5. An aerosol generating article for an aerosol generating device, the aerosol generating article defining a flow path from a heated air inlet for intake of a flow of heated air generated in use to an inhalable medium outlet, the aerosol generating article comprising:
   a container for containing a liquid;
   a wick downstream of the heated air inlet, the wick being for drawing the liquid from the container into the flow path, wherein the aerosol generating article is arranged such that, in use, the generated flow of heated air passes over the wick to volatilize the liquid to generate a flow of aerosol in the flow path; and
   a receiving portion in the flow path downstream of the wick, the receiving portion being for receiving an element for modifying a property of the flow of aerosol passing therethrough in use.

6. The aerosol generating article according to claim 5, wherein the aerosol generating article is arranged to be releasably connectable to the aerosol generating device.

7. The aerosol generating article according to claim 1, wherein the aerosol generating device is arranged such that, in use, the wick is heated only by convection.

8. The aerosol generating device according to claim 1, wherein the aerosol generating device is arranged such that the wick is blocked from radiation generated by the heating element in use.

9. The aerosol generating device according to claim 1, wherein the aerosol generating device comprises a shield element in the flow path, intermediate of the wick and the heating element for generating the flow of heated air in use, to shield the wick from the heating element.

10. The aerosol generating device according to claim 9, wherein the shield element comprises a first element extending across a first portion of a cross section of the flow path.

11. The aerosol generating device according to claim 10, wherein the shield element comprises a second element, downstream of the first element, extending across a second portion of the cross section of the flow path, wherein at least some of the second portion is different from the first portion.

12. The aerosol generating device according to claim 11, wherein the second portion comprises at least that portion of the cross section of the flow path across which the first element does not extend.

13. The aerosol generating device according to claim 9, wherein the shield element extends across an entire cross section of the flow path, and comprises one or more perforations to allow air to pass through the shield element.

14. The aerosol generating device according to claim 9, wherein a portion of the wick exposed to the flow of heated air generated in use is radially offset from a central longitudinal axis of the aerosol generating device.

15. The aerosol generating device according to claim 9, wherein the shield element blocks a line of sight from the heating element to the wick.

16. The aerosol generating device according to claim 1, wherein the container defines a channel running therethrough, and the channel defines at least a portion of the flow path.

17. The aerosol generating device according to claim 16, wherein at least a portion of the channel defines the receiving portion.

18. The aerosol generating device according to claim 1, wherein the receiving portion comprises one or more retaining elements for retaining the flavor element received in the receiving portion in use in the receiving portion.

19. The aerosol generating device according to claim 1, wherein the aerosol generating device is arranged so as to allow the element received in the receiving portion in use to be manually inserted or replaced in the receiving portion.

20. The aerosol generating device according to claim 1, wherein the wick comprises a metal mesh.

21. The aerosol generating device according to claim 1, wherein the aerosol generating device comprises an inlet controller to allow control of a flow of inlet air from the air inlet into the flow path.

22. The aerosol generating device according to claim 1, wherein the element comprises tobacco.

* * * * *

UNITED STATES PATENT AND TRADEMARK OFFICE
CERTIFICATE OF CORRECTION

PATENT NO. : 11,589,617 B2
APPLICATION NO. : 16/475571
DATED : February 28, 2023
INVENTOR(S) : Ugurhan Yilmaz It is certified that error appears in the above-identified patent and that said Letters Patent is hereby corrected as shown below:

In the Claims

Column 14, Line 65, in Claim 7, delete "article" and insert --device--.

Signed and Sealed this
Twenty-sixth Day of December, 2023

Katherine Kelly Vidal
Director of the United States Patent and Trademark Office